(12) United States Patent
Buettner

(10) Patent No.: US 6,722,182 B1
(45) Date of Patent: Apr. 20, 2004

(54) SOLID STATE VAPOR GENERATOR

(75) Inventor: Leonard C. Buettner, Baltimore, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/005,976

(22) Filed: Nov. 8, 2001

(51) Int. Cl.[7] .................. B01J 7/00; G01N 33/00; G01N 33/22
(52) U.S. Cl. .................. 73/1.03; 73/1.06; 422/305
(58) Field of Search ................... 422/305, 88–92; 73/1.03–1.07; 436/9

(56) References Cited

U.S. PATENT DOCUMENTS

| | | | | |
|---|---|---|---|---|
| 3,205,049 A | * | 9/1965 | Lannert et al. | 422/305 X |
| RE26,234 E | * | 7/1967 | Lightfoot | 264/41 |
| 4,069,701 A | * | 1/1978 | Baldauf et al. | 73/1.06 |
| 4,108,605 A | * | 8/1978 | Billings | 423/248 X |
| 4,151,739 A | * | 5/1979 | Breuer et al. | 73/1.06 |
| 4,372,915 A | * | 2/1983 | Neti et al. | 422/91 |
| 4,388,272 A | * | 6/1983 | Gesteland | 73/1.05 X |
| 5,326,546 A | * | 7/1994 | Rosenblatt et al. | 423/241 |
| 5,493,891 A | * | 2/1996 | Slemeyer | 436/9 X |
| 5,695,731 A | * | 12/1997 | Domergue et al. | 423/351 |
| 5,728,927 A | * | 3/1998 | Ong | 73/1.03 |
| 2001/0007304 A1 | * | 7/2001 | Izumi et al. | 204/262 |

FOREIGN PATENT DOCUMENTS

| | | | | |
|---|---|---|---|---|
| DE | 2427749 A1 | * | 2/1975 | B01J/7/00 |
| EP | 456527 A1 | * | 11/1991 | G01N/33/00 |
| EP | 816845 A1 | * | 1/1998 | G01N/33/00 |
| JP | 53-17385 | * | 2/1978 | 436/9 |
| JP | 2-111738 | * | 4/1990 | 427/255.19 |
| JP | 8-327508 | * | 12/1996 | G01N/33/00 |

* cited by examiner

Primary Examiner—Thomas P. Noland
(74) Attorney, Agent, or Firm—Ulysses John Biffoni

(57) ABSTRACT

A chemical adsorption system and method comprising an apparatus containing a solid adsorption article comprising a known amount of a chemical adsorbate material disposed on a solid adsorbent material. Trace amounts of the adsorbate are released from the adsorbent using an inert gas. By controlling various parameters such as the temperature of the adsorption article, the amount of the adsorbate on the adsorbent, and the flow rate of inert gas through the apparatus, the amount of chemical adsorbate material vapor that is released from the adsorbent can be precisely controlled and predicted. The apparatus contains no liquid chemical materials, and serves as both an internal chemical reference standard to the attached chemical vapor monitor and as a chemical surface passivator. Furthermore, the invention is capable of spanning several orders of magnitude in chemical vapor concentration from the parts-per-million (ppm) to parts-per-trillion (ppt) range.

17 Claims, 4 Drawing Sheets

SOLID STATE VAPOR GENERATOR

GOVERNMENT INTEREST

The invention described herein may be manufactured, licensed, and used by or for the U.S. Government.

BACKGROUND OF THE INVENTION

1. Field of the Invention

The present invention relates to chemical vapor generators. More particularly, it relates to a continuous, low-concentration, low-volume chemical solid state vapor generator (SSVG) apparatus and a solvent-free method for continuous surface passivation and controlled release of adsorbed chemical vapors from a solid adsorbent article. The apparatus is designed to be used in conjunction with, and for the calibration of, chemical air monitors and detectors known in the art for the collection, measurement, and quantitative analysis of chemical vapors.

2. Description of the Related Art

Chemical agent detection devices and monitors have been developed for use in various industries. These devices are often used for military purposes, to detect and quantify chemical agents such as HD or mustard gas, nerve agents such as GB and VX, and other highly toxic chemical vapors and aerosols.

Chemical vapor generator systems have been used in the art for calibrating and testing the agent sensitivity of such chemical agent devices and monitors. Several methods have been developed for performing such tests and calibrations. These methods typically involve the generation of chemical vapors using liquid chemical agents. U.S. Pat. No. 4,069,701 teaches a self-contained system for generating a dilute agent vapor of a desired concentration for use in calibrating and testing the sensitivity of an agent point-source alarm. Air is flowed through a dilute liquid agent solution in a bubbler, thus creating the desired vapor, which is then used to calibrate the alarm. U.S. Pat. No. 5,728,927 teaches a system for generating a chemical agent air stream for testing chemical agent detection devices. Liquid chemical agent is contained in a delta tube, which is immersed in a temperature bath to generate a chemical vapor stream. However, such methods are undesirable in that they can suffer from an uncontrolled release of the chemical agent, and the potential of aerosol formation exists if proper procedures are not carefully observed. These processes are also inherently dangerous due to the potential of an environmental release of chemical agents from the breakage of their chemical containing glass containers.

It is known in the art to use chemical vapor generator systems together with ambient air concentration monitors that continuously draw metered air samples to be analyzed for chemical vapor analysis through sampling lines connected to a chemical detector. Although much effort has been devoted to reducing surface adsorption and chemical reactivity of chemical vapors in these sampling lines, all sampling lines suffer from some form of chemical retention of material due to surface interactions between the chemical vapor of interest and the surface through which it passes. During periods of little or no chemical concentration activity, ambient air drawn through the chemical-vapor monitor will continuously strip away surface adsorbed chemical materials. This creates active adsorption sites throughout the entire sampling system. If the sampling line is then exposed to a transient chemical vapor concentration containing the chemical vapor of interest, a portion of this chemical will be removed from the air to passivate those previously exposed adsorption sites. This will result in an underestimation of the true chemical concentration of the original transient chemical exposure.

It would therefore be desirable to devise a continuous surface passivation apparatus and method for generating chemical vapors, which provides a chemical concentration standard for detector calibration that does not require the transport of liquid chemicals in the field. It would also be desirable for such an apparatus and method to be safe and accurate, and generate no chemical waste, thus reducing costs.

The present invention provides a solution to these problems. The invention provides a chemical adsorption system including chemical adsorption apparatus comprising a temperature-controlled, non-permeable, non-reactive container having vapor inlet and outlet fittings. The container contains a solid adsorption article, which comprises a known amount of a chemical adsorbate material disposed on a solid micro-porous adsorbent material. A controllable source of inert gas is connected to an inlet line on one end of the container, and an outlet line is connected to the other end of the container. By controlling various parameters such as the temperature of the adsorption article, the amount of the adsorbate on the adsorbent, and the flow rate of inert gas through the container, the amount of chemical adsorbate material vapor that is released from the adsorbent can be precisely controlled and predicted. This invention contains no liquid chemical materials in its design.

The invention solves the problem of surface passivation by continuously releasing a trace amount of chemical vapor in a small volume of inert gas to the sampling inlet of a chemical vapor concentration monitor or detector. In this arrangement, the apparatus of the invention serves as both an internal chemical reference standard to the attached chemical vapor monitor and as a chemical surface passivator. The apparatus thus continuously passivates all of the contacted surfaces with the chemical of interest, including the sample transfer line leading up to the attached chemical vapor monitor as well as the entire chemically exposed sampling surfaces contained within the chemical monitoring system itself. This allows for improved mass transport of chemical vapors in sampling systems. As an added benefit, all of the material exiting the container can be consumed by the air sampling monitoring system, thus generating no chemical waste.

The invention is further advantageous in that it serves to deliver an internal calibration standard from the adsorbent article for the purpose of calibrating air concentration monitors and detectors. Furthermore, the invention is capable of spanning several orders of magnitude in chemical vapor concentration from the parts-per-million (ppm) to parts-per-trillion (ppt) range.

SUMMARY OF THE INVENTION

The invention provides a chemical adsorption system, or solid state chemical vapor generator system, which comprises:

a) a chemical vapor generating apparatus comprising a temperature controlled housing having an outer shell defining an interior chamber; a vapor inlet disposed through a first end of the housing; a vapor outlet disposed through a second end of the housing; and an adsorption article which comprises a chemical adsorbate material disposed on a solid adsorbent material, which adsorption article is contained within a gas impermeable container within the interior chamber of the housing which container is attached to the vapor inlet and vapor outlet, and which adsorption article is capable of releasing controlled amounts of chemical adsorbate material vapor into the gas impermeable container;

b) an inert gas source connected to the vapor inlet via a vapor inlet tube, which gas source is capable of supplying a predetermined amount of inert gas into the interior chamber of the housing and into the gas impermeable container, via the vapor inlet; and c) a vapor outlet tube connected to the vapor outlet, through which vapor outlet tube the chemical adsorption apparatus is capable of releasing a predetermined amount of chemical vapor, together with a predetermined amount of inert gas, from the gas impermeable container and out of the housing.

The invention further provides a method for generating a chemical vapor gas stream, which comprises:

i) providing a chemical vapor generating system which comprises:
   a) a chemical adsorption apparatus comprising a temperature controlled housing having an outer shell defining an interior chamber; a vapor inlet disposed through a first end of the housing; a vapor outlet disposed through a second end of the housing; and an adsorption article which comprises a chemical adsorbate material disposed on a solid adsorbent material, which adsorption article is contained within a gas impermeable container within the interior chamber of the housing which container is attached to the vapor inlet and vapor outlet, and which adsorption article is capable of releasing controlled amounts of chemical adsorbate material vapor into the gas impermeable container;
   b) an inert gas source attached to the vapor inlet via a vapor inlet tube, which gas source is capable of supplying a predetermined amount of inert gas into the interior chamber of the housing via the vapor inlet; and
   c) a vapor outlet tube attached to the vapor outlet, through which vapor outlet tube the chemical adsorption apparatus is capable of releasing a predetermined amount of chemical adsorbate material vapor, together with a predetermined amount of inert gas, from the gas impermeable container and out of the housing; and ii) supplying a predetermined amount of inert gas from the inert gas source into the gas impermeable container; and wherein a predetermined amount of chemical adsorbate material vapor is released, together with a predetermined amount of inert gas, from the gas impermeable container and out of the housing, via the vapor outlet tube.

A solid-state chemical-vapor generating apparatus which comprises a temperature controlled housing having an outer shell defining an interior chamber; a vapor inlet disposed through a first end of the housing; a vapor outlet disposed through a second end of the housing; and an adsorption article which comprises a chemical adsorbate material disposed on a solid adsorbent material, which adsorption article is contained within a gas impermeable container within the interior chamber of the housing which container is attached to the vapor inlet and vapor outlet, and which adsorption article is capable of releasing controlled amounts of chemical adsorbate material vapor into the gas impermeable container.

DETAILED DESCRIPTION OF THE PREFERRED EMBODIMENT

The invention provides a chemical adsorption system for generating a chemical vapor gas stream. This chemical adsorption system comprises a chemical adsorption apparatus, which may serve as a chemical surface passivator and as an internal chemical reference standard to an attached chemical vapor detector.

Figure 1:
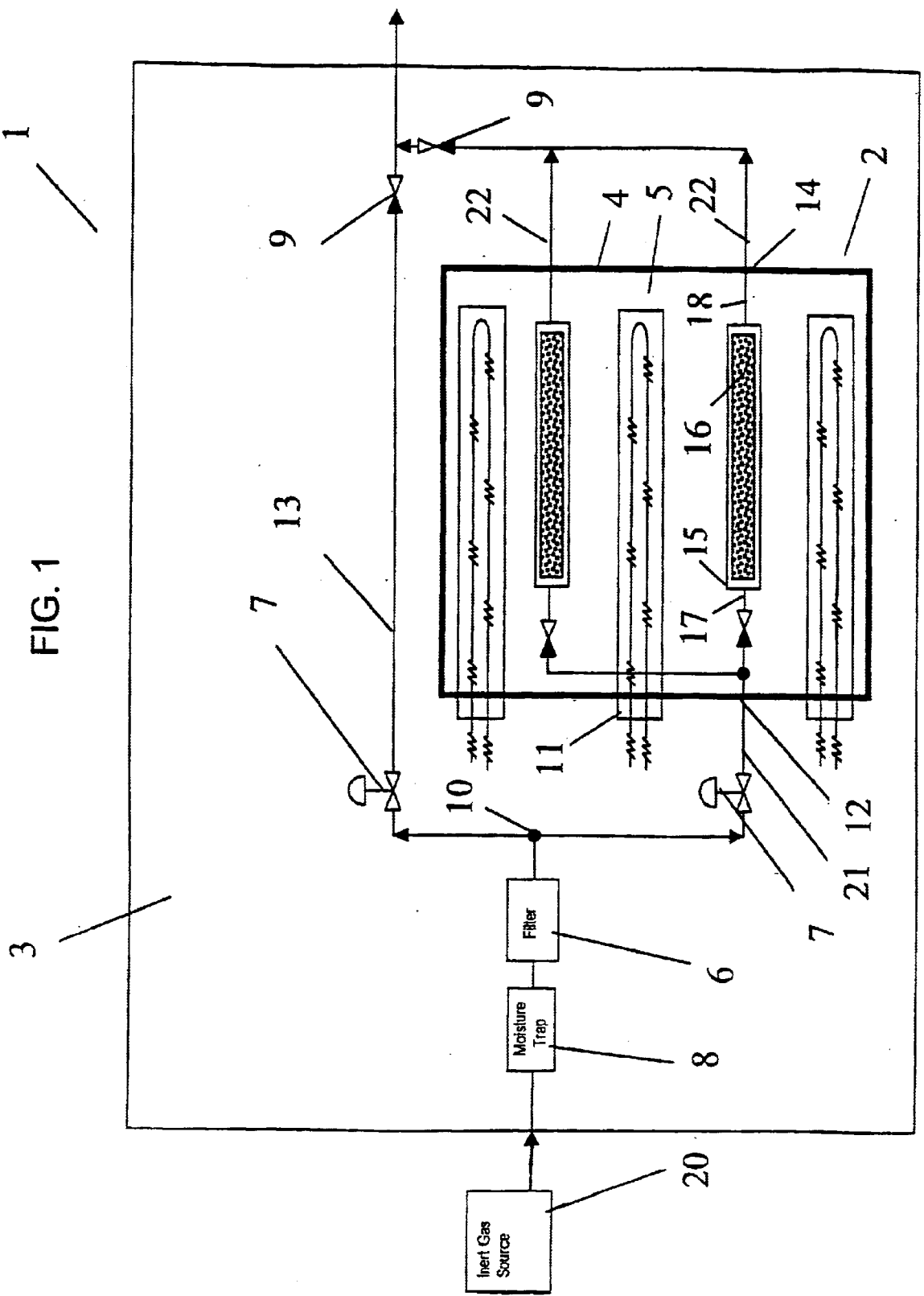
FIG. 1 shows a schematic diagram of a chemical adsorption apparatus of the invention.

FIG. 1 shows a schematic representation of one embodiment of the invention. FIG. 1 shows a chemical adsorption apparatus 1 which comprises a temperature controlled housing 2 within an optional protective casing 3. The temperature controlled housing 2 comprises an outer shell 4 defining an interior chamber 5. The outer shell 4 may comprise any material deemed suitable by those skilled in the art. Suitable materials of the outer shell 4 nonexclusively include metals, ceramics, glass, plastics, and the like. The outer shell 4 preferably comprises metal. The housing 2 may comprise any suitable shape such as a square or rectangular box, a cylinder, or the like. The optional protective casing 3 may comprise metal, plastic, or any other material suitable for forming a protective casing, and may comprise any suitable shape such as a square or rectangular box, a cylinder, or the like.

The housing 2 and the optional protective casing 3, if present, may each comprise one or more additional optional features (shown in FIG. 1) such as an internal filter 6, mass flow controllers 7, moisture trap 8, valves 9, switches 10, tubing 13 and the like, which may be connected to any components of apparatus 1 and/or to other optional components of the chemical adsorption system.

The housing 2 is preferably temperature-controlled in order to regulate the rate of desorption of an adsorption article, as described below, which is to be situated within the housing 2. The temperature of the housing 2 may be controlled using any suitable means known in the art such as on-off controls, proportional controls, proportional with integral and derivative (PID) controllers, and the like. As shown in FIG. 1, the housing 2 preferably comprises internal heaters 11 for controlling the temperature within the interior chamber 5 of the housing 2. Such internal heaters 11 may comprise any conventional heating means deemed suitable by those skilled in the art, such as a cartridge heater, strip heater, tubular heating elements and the like.

A vapor inlet 12 is disposed through a first end of the housing 2, and a vapor outlet 14 is disposed through a second end of the housing 2, as depicted in FIG. 1. The vapor inlet 12 serves to allow gas or other vapors to enter into the interior chamber 5 of the housing 2. The vapor outlet 14 serves to allow gas or other vapors to be expelled from the interior chamber 5 of the housing 2.

A gas impermeable container 15 is situated within the interior chamber 5 of the housing 2, which container 15 is attached via tubing to the vapor inlet 12 and the vapor outlet 14. The container 15 preferably comprises any suitable material which is impermeable to gas, and which is thermally conductive. Suitable materials for the gas impermeable container 15 nonexclusively include metal, glass, plastic and the like. The gas impermeable container 15 may comprise a sorbent tube, also known in the art as a packed adsorbent bed. Such packed adsorbent beds are available commercially from SKC of Pennsylvania, USA The gas impermeable container 15 is preferably attached to the vapor inlet 12 via a container entry tube 17, and is attached to the vapor outlet 14 via a container exit tube 18. The container entry tube 17 and container exit 18 tube may comprise any suitable tubing material such as plastic, rubber, glass, metal or Teflon®, which is available commercially from DuPont, or combinations thereof. Preferably, the container entry tube 17 and container exit 18 tube each comprise metal.

An adsorption article 16 is formed, as described below, and packed within the gas impermeable container 15. The adsorption article 16 comprises a chemical adsorbate material disposed on a solid adsorbent material. The adsorption article 16 is capable of desorbing, or releasing, controlled amounts of the chemical adsorbate material vapor into the gas impermeable container 15. Such vapors may then be released from the gas impermeable container 15 and used for chemical surface passivation, or as an internal chemical reference standard to a chemical vapor monitor or the like.

Suitable solid adsorbent materials include both inorganic and organic adsorbent materials, which are well known in the art to be used as adsorbents such as activated synthetic and non-synthetic carbons, silicas, aluminas, and the like, and combinations thereof Preferably, the solid adsorbent material comprises activated synthetic carbon. The solid adsorbent material may comprise any suitable shape ranging from a single flat substrate to spherical particles or the like. It is most preferred that the solid adsorbent material comprises a micro-porous material. Suitable solid adsorbent materials may be purchased commercially, and nonexclusively include Ambersorb™ (activated synthetic carbon) from Rohm & Haas Corp. of Philadelphia, Pa., USA; and BPL Carbon™ (activated non-synthetic carbon), from Calgon Carbon Corp. of Huntington, W. Va., USA.

Suitable chemical adsorbate materials include any chemical material which is to be measured, tested for, or detected using a chemical air monitor or chemical vapor detector or other similar apparatus. It is most preferred that the chemical adsorbate material does not react with the solid adsorbent material. It is also preferable that the chemical adsorbate material has a pure component vapor pressure above about 0.01 Pa at about 25° C. Suitable chemical adsorbate materials nonexclusively include chemical nerve agents, toxic industrial chemicals, narcotics, explosives and the like, which are to be tested for or detected at or near military bases, battlefields, chemical manufacturing facilities, airports, factories, buildings, homes, vehicles, and the like. Examples of suitable chemical adsorbate materials nonexclusively include biological and chemical warfare agents, for example, chemical nerve agents such as HD, also known as mustard or bis-(2-chloroethyl) sulfide; GA, also known as tabun or ethyl N, N-dimethylphosphoroamidocyanidate; GB, also known as sarin or isopropyl methyl phosphofluoridate; GD, also known as soman or pinacolyl methyl phosphonofluoridate; GF, also known as O-cyclohexylmethylphosphonofluoridate, and VX, also known as O-ethyl S-(2-diisopropylaminoethyl) methyl phosphonothioate; toxic industrial chemicals such as pesticides, chlorinated dioxins and furans; narcotics such as methamphetomines including PCP, or phencyclidine; LSD or lysergic acid diethylamide; and explosives such as DNT or dinitrotoluene; TNT or trinitrotoluene; and other chemicals which are known in the art as chemical warfare agents, toxic industrial chemicals, narcotics, and explosives. One preferred material for the chemical adsorbate material comprises HD, also known as bis-(2-chloroethyl) sulfide.

In one preferred embodiment, the chemical adsorption apparatus comprises at least one additional gas impermeable container packed with an additional adsorption article. Such additional packed containers, if present, may comprise a chemical adsorbate material and a solid adsorbent material which are each independently the same or different than the adsorption article in the first container.

The adsorption article 16 is preferably formed by depositing vapors of a chemical adsorbate material onto a solid adsorbent material substrate. It is important that the chemical adsorbate material is uniformly distributed among and at equilibrium with the adsorbent material. Failure to achieve an equilibrated, uniformly loaded, non-reactive adsorbate coating on the solid adsorbent material may result in unstable desorption, variable output concentrations of chemical vapors, or both.

The adsorption article may be formed using any suitable chemical loading or deposition method known to those skilled in the art for forming an adsorption article having the features described above. One preferred method comprises the slow (less than about 0.1 ul/min) evaporation of the chemical adsorbate into a fluidized bed of adsorbent operated at above ambient temperatures.

Figure 2:
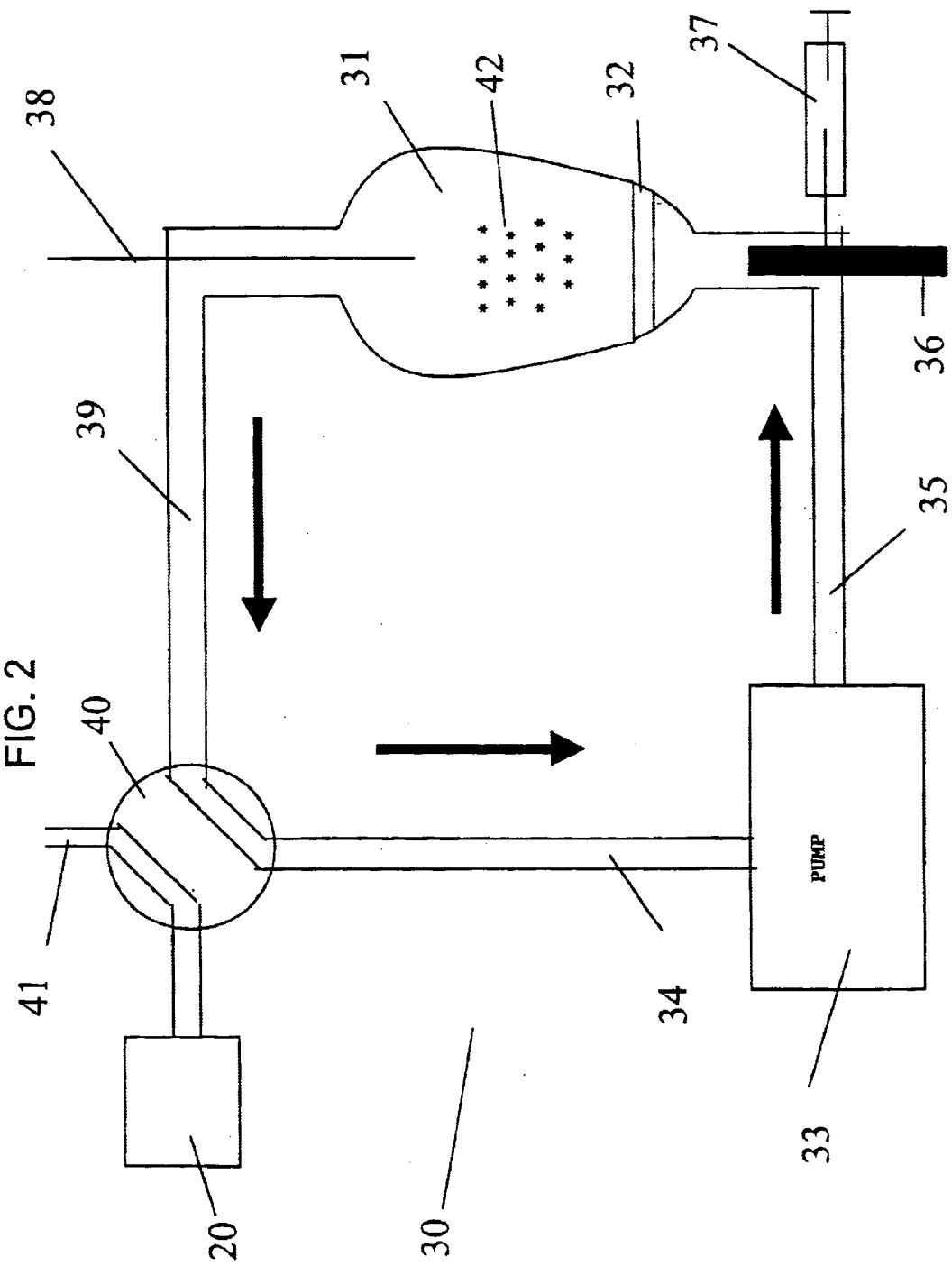
FIG. 2 shows a schematic diagram showing the formation of an adsorption article of the invention.

FIG. 2 shows a schematic representation of one preferred method for forming the adsorbent article. According to FIG. 2, a closed-loop circulating system 30 includes a glass vessel 31, which contains fluidized solid adsorbent material particles 42 suspended above a porous glass frit 32. Inert gas from an inert gas source 20 is initially allowed to purge through the system 30 by way of a 4-way valve 40. Suitable inert gases nonexclusively include helium, hydrogen, nitrogen, neon, argon, krypton, xenon, radon, and the like, and combinations thereof. Prior to introducing an adsorbate material into the system, the inert gas enters into the system 30 through the 4-way valve 40 (open position not shown in FIG. 2), circulates through the pump 33 and glass vessel 31 to dry the solid adsorbent particles 42 and the system 30, and then exits the system through the vent 41. The valve 40 is then positioned in a closed-loop configuration as shown in FIG. 2 to begin a loading of the adsorbate material onto the solid adsorbent particles. The pump 33 circulates the inert gas through a vessel entry tube 35 and into a bottom of the glass vessel 31. The inert gas is heated within the vessel entry tube 35 by a heating element 36 as it enters the bottom of the glass vessel 31. A syringe pump 37, which contains a liquid chemical adsorbate material, is then used to inject the liquid chemical adsorbate material into the vessel entry tube 35, thus combining it with the heated inert gas. As both the heated inert gas and the liquid chemical adsorbate enter the glass vessel 31, the liquid chemical adsorbate material becomes vaporized. Once inside the glass vessel 31, the temperatures of the vaporized adsorbate and the solid adsorbent material particles 42 are measured with a temperature sensor 38, which is present inside the glass vessel 31. Temperature conditions within the glass vessel 31 are controlled such that the vaporized adsorbate becomes uniformly loaded onto the adsorbent material particles 42. Any remaining inert gas in the system 30 is then directed out of the glass vessel 31 via a vessel output tube 39, through valve 40, and back to pump 33 by the pump entry tube 34. The adsorption article formed by the system 30 is packed into a gas impermeable container 15, as described above and shown in FIG. 1, to form an adsorption article 16 as defined above.

Figure 3:
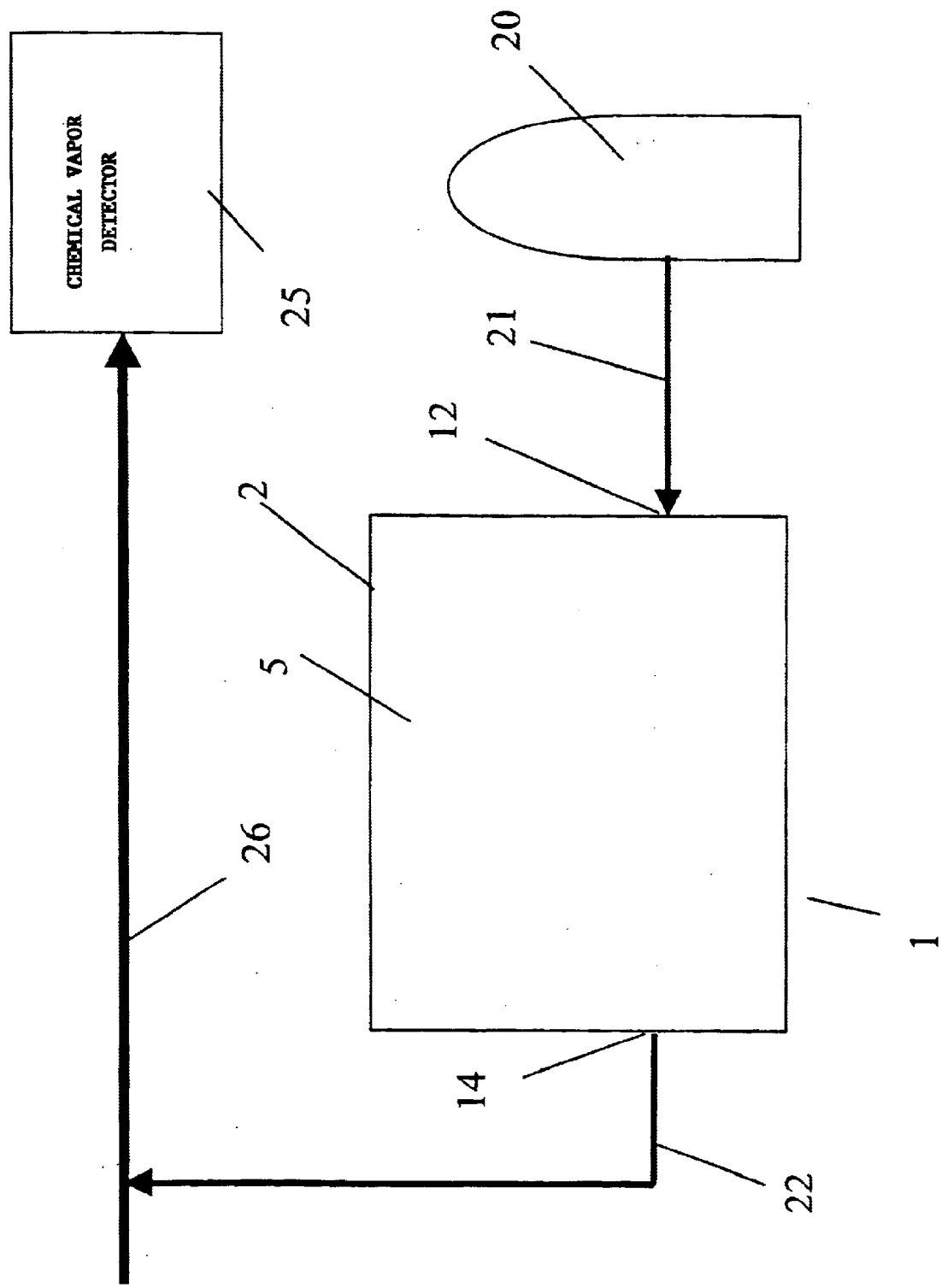
FIG. 3 shows a block diagram of a chemical adsorption system of the invention, which includes a chemical adsorption apparatus connected to a chemical vapor detector device.

FIG. 3 shows a chemical adsorption system according to one preferred embodiment of present invention. According to FIG. 3, an inert gas source 20 is connected to the vapor inlet 12 of the chemical adsorption apparatus 1 via a vapor inlet tube 21. The inert gas source 20 is capable of supplying a predetermined amount of inert gas into the interior chamber 5 of the housing 2 via the vapor inlet 12. The vapor inlet tube 21 may comprise any suitable material such as plastic, rubber, glass, metal or Teflon®, and combinations thereof Preferably, the vapor inlet tube 21 comprises metal. Suitable inert gases nonexclusively include helium, hydrogen, nitrogen, neon, argon, krypton, xenon, radon, and the like, and combinations thereof.

A vapor outlet tube 22 is connected to the vapor outlet 14 of the chemical adsorption apparatus 1. The vapor outlet tube 22 is capable of releasing a predetermined amount of chemical vapor, together with a predetermined amount of inert gas, from the interior chamber 5 of the housing 2. The vapor outlet tube 22 may also comprise any suitable material such as plastic, rubber, glass, metal, or Teflon®, and combinations thereof. Preferably, the vapor outlet tube 22 comprises metal.

A chemical air monitoring device, or chemical vapor detector, 25 is connected to the chemical adsorption apparatus 1. The chemical vapor detector 25 may be connected to the apparatus 1 via the vapor outlet tube 22. In a most preferred embodiment, the chemical vapor detector 25 is connected to the vapor outlet tube 22 via a sampling line 26 attached to the chemical vapor detector 25. Chemical vapor detectors and chemical air monitors are known in the art and are available commercially from CDS Analytical, Inc. of Oxford, Pa., USA; and Agilent Technologies of Palo Alto, Calif., USA. The chemical adsorption system of the invention may optionally be interfaced to a gas chromatograph, mass spectrometer, atomic emission detector, or any other analytical vapor detector deemed suitable by those skilled in the art.

To generate a chemical vapor gas stream according to the invention, a predetermined amount of inert gas is supplied from the inert gas source 20 into the interior chamber 5 of the housing 2, as described above. Once inside the housing 2, the inert gas enters the gas impermeable container 15 and contacts the adsorbate-adsorbent material of the adsorption article 16 under conditions sufficient to thereby cause a predetermined amount of chemical adsorbate material to be displaced from the solid adsorbent material of the adsorption article, in the form of a vapor. A predetermined amount of chemical adsorbate material vapor, together with a predetermined amount of inert gas, is then released from the gas impermeable container 15 and is then released from the interior chamber 5 of the housing 2 via the vapor outlet tube 22.

The chemical adsorption system of the present invention is preferably capable of generating a wide range of chemical vapor concentrations, ranging from about 100 parts per million (ppm) to about 1 part per trillion (ppt) in an inert carrier stream without dilution. This may be achieved by controlling the mass loading of the chemical adsorbate material onto the solid adsorbent material and controlling the temperature and inert carrier flow rate which affects the adsorbent article. Such parameters may be sufficiently controlled by one skilled in the art.

In one preferred embodiment an optional dilution stream is used, which dilution stream is flowed through tubing 13, as shown in FIG. 1. Although the apparatus can be used without the optional dilution stream to produce a wide range of chemical vapor concentrations through changes in the temperature of the housing 2 and hence the packed gas impermeable container 15 which houses the adsorption article 16, such temperature changes require equilibration time. Thus, another alternative would be to vary the chemical concentration of the vapors exiting the apparatus 1 by keeping the temperature constant and selecting between different gas impermeable containers, each containing an adsorption article having varying amounts of the chemical adsorbate uniformly loaded onto the adsorbent material; or varying the inert gas flow through the adsorption articles; or both.

A chemical adsorption apparatus 1 of the invention, which is attached to a chemical vapor detector, air sampling device, or the like such, may serve as an internal chemical reference standard for chemical testing operations.

The following non-limiting example serves to illustrate the invention. It will be appreciated that variations in proportions and alternatives in elements of the components of the invention will be apparent to those skilled in the art and are within the scope of the present invention.

EXAMPLE 1

Figure 4:
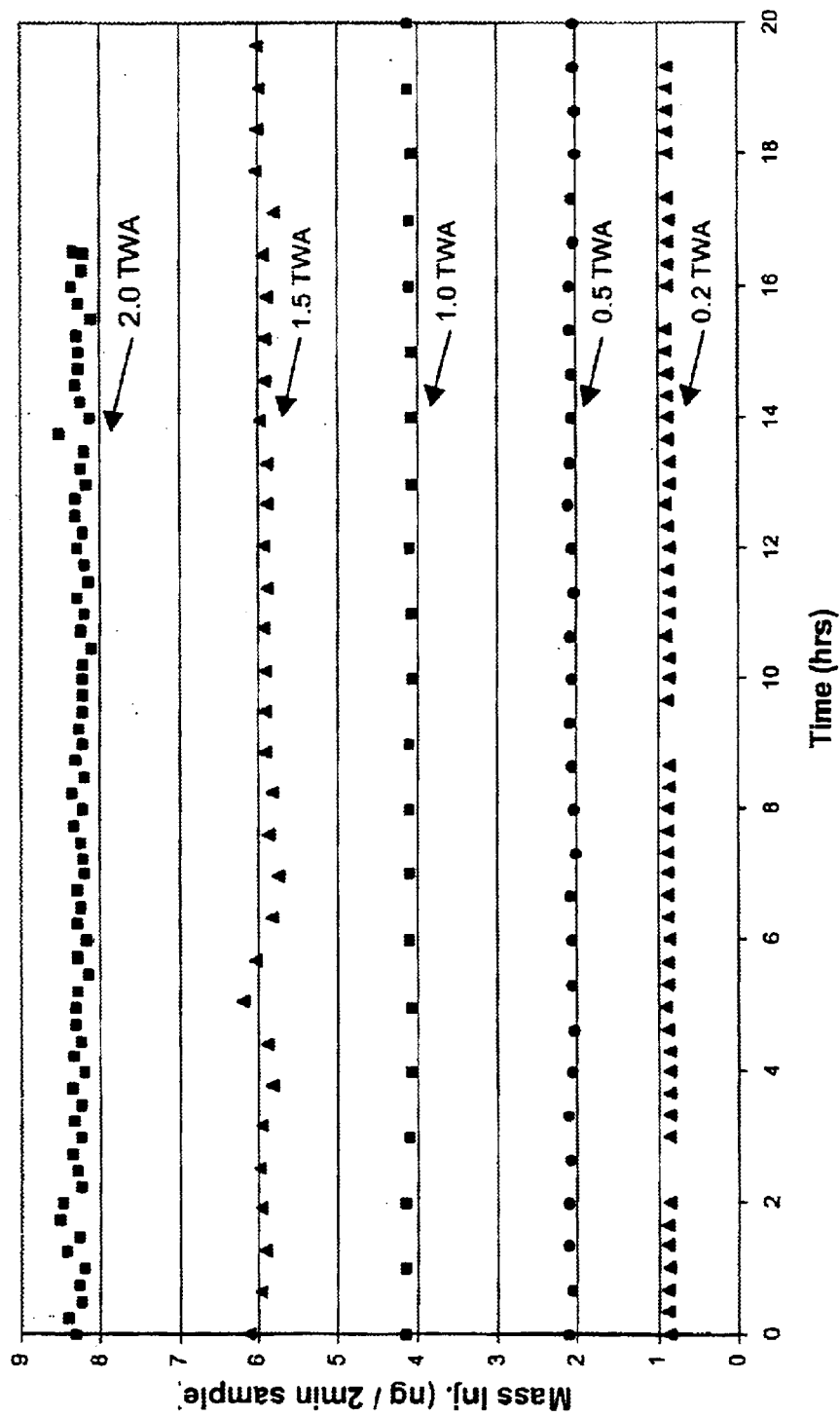
FIG. 4 shows a chart of experimental data from a prototype Mustard, HD (bis-2-chloroethylsulfide) generator.

A chemical adsorption apparatus 1 was built as described above and as shown in FIG. 1, and attached to an inert gas source 20 and a chemical vapor detector 25 as shown in FIG. 3. FIG. 4 shows experimental data from a prototype Mustard, HD (bis-2-chloroethylsulfide) generator.

An adsorption article 16, shown in FIG. 1 and described above, was prepared according to the specifications described above and as shown in FIG. 2, using a 10.4% chemical loading of HD (bis-2-chloroethylsulfide) uniformly distributed on Ambersorb 563 adsorbent substrate. Dry helium gas was used as the inert carrier gas and the adsorbent temperature was maintained at 125° C. The HD was dispensed from a syringe-driven pump at a rate of 0.1 $\mu$l/min. Fluidization of the substrate at this temperature was continued for an additional 24 hours to help promote a substantially uniform distribution of the adsorbate throughout the adsorbent. Approximately 2 grams of the adsorbent was transferred to two empty metal sorbent tubes and constrained between two sintered-metal frits.

Following the transfer of these tubes into a chemical adsorption apparatus described in FIG. 1, the desorption temperature was determined to be at 56° C. to deliver a 1.0 AEL-TWA (Airborne Exposure Limit-Time Weighted Average) of HD (0.003 mg/m$^3$) in a 800 sccm (standard cubic centimeters per minute) flow stream to an air monitor using a 50 sccm nitrogen sorbent-tube flow and a 50 sccm nitrogen dilution flow. The temperature of the sorbent-tubes was kept constant and the ratio of the flow rate between the sorbent-tube flow and the dilution flow were varied to change the output concentrations. As an example, if the 0.2 AEL-TWA setting required 10% or 10 sccm flow through the selected sorbent tube and 90% or 90 sccm from the dilution mass flow controller, then a 2.0 AEL-TWA setting would require a sorbent-tube flow setting of 100% or 100 sccm and no dilution flow. The total output flow from the apparatus was fixed at 100 sccm and the sample-line inlet flow to the chemical vapor detector was set at 800 sccm.

The low-volume, low-concentration output from the chemical adsorption apparatus was needed to passivate the sampling line leading to the chemical vapor detector, in this case a HP 5890 Gas Chromatograph equipped with a Flame Photomeric Detector operating in the sulfur mode and a Dynatherm-ACEM 900 chemical vapor concentrator. The step change in concentration from the 0.2 to 2.0 AEL-TWA illustrates both the stability of this chemical adsorption apparatus and the predictability of the apparatus to calculate new conditions to meet the desired concentration. The apparatus was capable of continuously delivering AEL-TWA levels of HD to a chemical vapor detector, and serving as an internal standard of HD to the detector.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above, and all equivalents thereto.

What is claimed is:

1. A solid-state chemical vapor generator, comprising:

(a) a housing having a vapor inlet and a vapor outlet;

(b) means for controlling the temperature within said housing;

(c) at least one gas impermeable, thermally conductive container disposed within said housing, wherein a first end of said at least one gas impermeable container is connected to said vapor inlet and a second end of said at least one gas impermeable container is connected to said vapor outlet;

(d) an adsorption article contained within said at least one gas impermeable, thermally conductive container, said adsorption article comprising a chemical adsorbate material substantially uniformly distributed on and at equilibrium with an adsorbent material, such that said adsorption article releases a controlled amount of chemical adsorbate vapor into said gas impermeable container based on the temperature maintained in said housing; and (e) means for introducing a continuous flow of an inert gas into said vapor inlet, through said at least one gas impermeable container, and out said vapor outlet, thereby delivering a continuous flow of controlled concentration of chemical adsorbate vapor, wherein said concentration of chemical adsorbate vapor is determined by the temperature maintained in said housing, the amount of the chemical adsorbate uniformly applied to said absorbent, and the flow rate of inert gas through said at least one gas impermeable container.

2. The solid-state chemical vapor generator of claim 1, further comprising a protective casing surrounding said housing, said protective casing having a vapor inlet and a vapor outlet operably connected to said housing vapor inlet and said housing vapor outlet, respectively.

3. The vapor generator of claim 2, wherein said protective casing comprises a material selected from the group consisting of metals and plastics.

4. The vapor generator of claim 1, wherein said housing comprises a material selected from the group consisting of metals, ceramics, glass, and plastics.

5. The vapor generator of claim 1, further comprising a filter and a moisture trap operably positioned between said means for introducing an inert gas and said housing vapor inlet.

6. The vapor generator of claim 1, wherein said at least one gas impermeable, thermally conductive container comprises a plurality of gas impermeable, thermally conductive containers, wherein each of said containers have different amounts of said chemical adsorbate material loaded onto said adsorbent material.

7. The vapor generator of claim 1, wherein said means for controlling temperature within said housing is capable of adjusting the temperature within said housing between the prevailing ambient temperature and the thermal decomposition temperature of the adsorbent-adsorbate pair.

8. The vapor generator of claim 7, wherein said means for controlling temperature comprises controlled heating means disposed within said housing, said heating means selected from the group consisting of cartridge heaters, strip heaters, and tubular heating elements.

9. The vapor generator of claim 1, wherein said gas impermeable container comprises a sorbent tube.

10. The vapor generator of claim 9, wherein said sorbent tube includes a solid adsorbent material selected from the group consisting of activated non-synthetic carbon, activated synthetic carbon, silicas, aluminas, and combinations thereof.

11. The vapor generator of claim 10, wherein said solid adsorbent material comprises a micro-porous material.

12. The vapor generator of claim 1, wherein said chemical adsorbate material is selected from the group consisting of chemical warfare agents, toxic industrial chemicals, narcotics, and explosives.

13. The vapor generator of claim 1, wherein said vapor generator is capable of continuously delivering an adsorbate chemical vapor in an inert gas over a range of concentrations from about 100 parts per million (ppm) to about 1 part per trillion (ppt).

14. The vapor generator of claim 1, wherein said vapor generator is capable of continuously delivering a low volume of adsorbate chemical vapor in inert gas, wherein said volumes are less than 250 sccm.

15. The vapor generator of claim 1, further comprising a chemical air monitoring device connected to the vapor outlet of said housing, so that said vapor generator continuously passivates all surfaces in contact with chemical adsorbate vapor flow.

16. The vapor generator of claim 15, wherein said vapor generator serves as an internal calibration device for said chemical air monitoring device.

17. The vapor generator of claim 1, further comprising means for providing a dilution stream of inert gas to said adsorbate chemical vapor flow after said adsorbate chemical vapor flow exits said at least one gas impermeable container, so that said dilution stream can be used to vary the adsorbate chemical vapor concentration.

* * * * *